US006667377B2

(12) United States Patent
Feiring et al.

(10) Patent No.: US 6,667,377 B2
(45) Date of Patent: *Dec. 23, 2003

(54) POLYVINYLIDENE FLUORIDE IONOMERS CONTAINING PENDANT FLUOROALKYLSULFONYL IMIDE OR FLUOROALKYLSULFONYL METHIDE GROUPS

(75) Inventors: Andrew Edward Feiring, Wilmington, DE (US); Christopher Marc Doyle, Newark, DE (US); Mark Gerrit Roelofs, Hockessin, DE (US); William Brown Farnham, Newark, DE (US); Paul Gregory Bekiarian, Wilmington, DE (US); Hanne A. K. Blau, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/852,381

(22) Filed: May 10, 2001

(65) Prior Publication Data
US 2002/0045713 A1 Apr. 18, 2002

Related U.S. Application Data

(63) Continuation-in-part of application No. 09/260,204, filed on Mar. 2, 1999, now abandoned.
(60) Provisional application No. 60/076,578, filed on Mar. 3, 1998.

(51) Int. Cl.$^7$ .................. C08F 12/30; C08F 214/22; C08L 27/16
(52) U.S. Cl. .................. 526/240; 526/241; 526/243; 525/326.2; 525/362; 525/366; 525/367; 525/368; 525/369; 524/544; 524/379; 524/280

(58) Field of Search .................. 526/240, 241, 526/243; 525/326.2, 362, 366, 367, 368, 369; 524/544, 379, 280

(56) References Cited

U.S. PATENT DOCUMENTS

| 3,282,875 A | 11/1966 | Connolly et al. |
| 4,818,644 A | 4/1989 | Armand |
| 4,940,525 A | 7/1990 | Ezzell et al. |
| 5,463,005 A | 10/1995 | Desmarteau |
| 5,696,224 A | 12/1997 | Benrabah et al. |
| 6,287,722 B1 * | 9/2001 | Barton et al. ............ 429/176 |
| 6,395,838 B1 * | 5/2002 | Rodriguez-Parada ........ 525/200 |

FOREIGN PATENT DOCUMENTS

| JP | 9-263637 | 10/1997 |
| JP | 98168194 | 6/1998 |
| JP | 0850920 A2 | 7/1998 |
| JP | 0850921 A1 | 7/1998 |

OTHER PUBLICATIONS

Xue, Lixin, Chemistry of Bis (Perfluoroalkylsulfonyl)imides and Related Compounds, Dissertation, 101–107, Aug., 1996.

Schmiegel, W.W., Crosslinking of Elastomeric Vinylidene Fluoride Copolymers with Nucleophiles, Die. Angewandte Makromolekulare Chemie, 76, 77, 39–65, 1979.

D. D. Desmarteau, Novel Perfluorinated Ionomers and Ionenes, Journal of Fluorine Chemistry, 72 (2), 203–208, Jun. 1995.

* cited by examiner

Primary Examiner—Donald R. Wilson

(57) ABSTRACT

This invention concerns ionomers comprising monomer units of vinylidene fluoride and monomer units of perfluorovinyl ethers having pendant groups containing fluoroalkyl sulfonyl methide or fluoroalkyl sulfonyl imide derivatives and univalent metal salts thereof, and with the uses of said ionomers in eledrochemical applications, electrochemical capacitors and modified electrodes.

30 Claims, No Drawings

POLYVINYLIDENE FLUORIDE IONOMERS CONTAINING PENDANT FLUOROALKYLSULFONYL IMIDE OR FLUOROALKYLSULFONYL METHIDE GROUPS

FIELD OF THE INVENTION

This invention deals with substantially fluorinated but not perfluorinated ionomers, and related ionic and nonionic monomers, having pendant groups containing fluorosulfonyl methide or fluorosulfonyl imide derivatives and univalent metal salts thereof, and with the uses of said ionomers in electrochemical applications such as batteries, fuel cells, electrolysis cells, ion exchange membranes, sensors, electrochromic windows, electrochemical capacitors, and modified electrodes. Certain compositions of the invention are also useful as strong acid catalysts.

BACKGROUND OF THE INVENTION

Copolymers of vinylidene fluoride (VF2) with vinyl alkoxy sulfonyl halides are known in the art.

The disclosures in Ezzell et al. (U.S. Pat. No. 4,940,525) encompass copolymers of VF2 with vinyl ethoxy sulfonyl fluorides containing one ether linkage. Disclosed is a process for emulsion polymerization of tetrafluoroethylene (TFE) with the vinyl ethoxy comonomer.

Connolly et al. (U.S. Pat. No. 3,282,875) disclose the terpolymer of VF2 with perfluorosulfonyl fluoride ethoxy propyl vinyl ether (PSEPVE) and hexafluoropropylene (HFP). They broadly teach an emulsion polymerization process said to be applicable to copolymerization of vinyl ethers with any ethylenically unsaturated comonomer, with greatest applicability to fluorinated monomers.

DesMarteau (U.S. Pat. No. 5,463,005), incorporated herein by reference, discloses substituted perfluoro-olefins of the formula

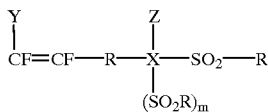  (I)

where X=C or N, Z=H, K, Na, or Group I or II metal, R=one or more fluorocarbon groups including fluorocarbon ethers and/or sulfonyl groups and/or perfluoro non-oxy acid groups, Y=perfluoroalkyl or F, and m=0 or 1. Further disclosed by DesMarteau are copolymers formed by aqueous emulsion polymerization of the sodium salt form of (I) with tetrafluoroethylene. Further disclosed are compositions consisting of the acid-form of the imide copolymer of DesMarteau in combination with dimethylformamide (hereinafter DMF) to provide a conductive composition. Membranes or films of the acid imide polymer are cast from solution. Copolymers of the substituted perfluoroolefins with VF2 are not disclosed in U.S. Pat. No. 5,463,005.

Armand (U.S. Pat. No. 4,818,644) discloses metal salts based on anions having the structure $R_f$—$SO_2CR$—$SO_2R'_f$ where $R_f$ and $R'_f$ are perfluorinated groups having from 1 to 10 carbon atoms and R is a hydrogen or an alkyl group having from 1 to 30 carbon atoms. The lithium salts of these compounds are useful in combination with organic solvents or macromolecular solvents for making electrolyte solutions for lithium batteries. Armand et al. further disclose (EP 0 850 921) salts and ionomeric polymers derived from malononitrile Z—C(CN)2 where Z represents an electron-withdrawing group and Z can also contain a polymerizable function. Ionomers based on these compounds are disclosed having styrenic or vinyl functional groups for polymerization. Copolymers of these monomers with substantially fluorinated monomers such as VF2 are not disclosed.

Xue, Ph.D. thesis, Clemson University, 1996, discloses reactions of the type $RSO_2NHX$ with $R'SO_2Y$ with X=H, Na and Y=Cl, F to form $RSO_2N(M)SO_2R'$, where R and R' are perfluorinated groups, in the presence of MF with M=Cs, K or in the presence of $Na_2CO_3$ if X=Na and Y=Cl to form monomers represented by the formula

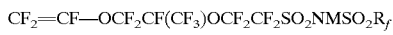

and copolymers thereof with tetrafluoroethylene.

Armand et al, EP0850921A1 and EP0850920A1, provide a tremendous list of imide- and methide-containing ionic species, including polymers incorporating them. However, no means for making these compositions is provided, and no distinction is made among the compounds from the standpoint of utility. No disclosure is made of the particular utility and surprising attributes of the compositions of the present invention.

SUMMARY OF THE INVENTION

The present invention provides for an ionic polymer (ionomer) comprising monomer units of VF2 and further comprising 0.5–50 mol-% of monomer units having pendant groups comprising the radical represented by the formula

   (I)

wherein

R and R' are independently selected from F, Cl or a perfluoroalkyl group having 1 to 10 carbon atoms optionally substituted by one or more ether oxygens;

a=0, 1 or 2;

b=0 to 6;

$M^+$ is $H^+$ or a univalent metal cation;

X is C or N with the proviso that c=1 when X is C and c=0 when X is N; when c=1, Y and Z are electron-withdrawing groups selected from the group consisting of CN, $SO_2R_f$, $SO_2R^3$, $P(O)(OR^3)_2$, $CO_2R^3$, $P(O)R^3_2$, $C(O)R_fC(O)R^3$, and cycloalkenyl groups formed therewith wherein $R_f$ is a perfluoroalkyl group of 1–10 carbons optionally substituted with one or more ether oxygens;

$R^3$ is an alkyl group of 1–6 carbons optionally substituted with one or more ether oxygens, or an aryl group optionally further substituted;

Y and Z are the same or different;

or, when c=0, Y may be an electron-withdrawing group represented by the formula —$SO_2R_f'$ where $R_f'$ is the radical represented by the formula —$(R_f''SO_2N^-(M^+)SO_2)_mR_f'''$ where m=0 or 1, and $R_f''$ is —$C_nF_{2n}$— and $R_f'''$ is —$C_nF_{2n+1}$ where n=1–10, optionally substituted with one or more ether oxygens.

The present invention further provides for an ethylenically unsaturated composition represented by the formula

   (II)

wherein

R and R' are independently selected from F, Cl or a perfluoroalkyl group having 1 to 10 carbon atoms optionally substituted with one or more ether oxygens;

a=0, 1 or 2;

b=0 to 6;

$M^+$ is $H^+$ or a univalent metal cation;

Y and Z are electron-withdrawing groups selected from the group consisting of CN, $SO_2R^3$, $P(O)(OR^3)_2$, $CO_2R^3$, $P(O)R^3{}_2$, $C(O)R_fC(O)R^3$, and cycloalkenyl groups formed therewith wherein $R_f$ is a perfluoroalkyl group of 1–10 carbons optionally substituted with one or more ether oxygens;

$R^3$ is an alkyl group of 1–6 carbons optionally substituted with one or more ether oxygens, or an aryl group optionally further substituted;

Y and Z are the same or different.

The present invention further provides a method for making a methide ionomer the method comprising, combining in an inert organic liquid at a temperature in the range of 0–150° C. a copolymer comprising monomer units of VF2 and 0.5–50 mol-% of monomer units represented by the formula:

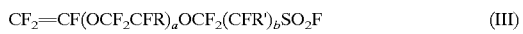
$$CF_2=CF(OCF_2CFR)_aOCF_2(CFR')_bSO_2F \quad (III)$$

wherein R and R' are independently selected from F, Cl or a perfluoroalkyl group having 1 to 10 carbon atoms optionally substituted with one or more ether oxygens, a=0, 1 or 2, and b=0 to 6; with a carbanion derived from a methylene compound represented by the formula $CH_2YZ$ wherein Y and Z are electron-withdrawing groups selected from the group consisting of CN, $SO_2R_f$, $SO_2R^3$, $P(O)(OR^3)_2$, $CO_2R^3$, $P(O)R^3{}_2$, $C(O)R_fC(O)R^3$, and cycloalkenyl groups formed therewith, wherein $R_f$ is a perfluoroalkyl group of 1–10 carbons, optionally substituted with one or more ether oxygens, $R^3$ is an alkyl group of 1–6 carbons, optionally substituted with one or more ether oxygens or an aryl group optionally further substituted; and wherein Y and Z may be either the same or different to form a reaction mixture; reacting said reaction mixture until the desired degree of conversion has been achieved; and, removing the majority of said organic liquid.

The present invention further provides a method for making a methide composition the method comprising, combining an inert organic solvent at a temperature in the range of 0–100° C. a composition represented by the formula $$CF_2A\text{---}CFA(OCF_2CFR)_aOCF_2(CFR')_bSO_2F \quad (IV)$$

wherein A is Br or Cl, R and R' are independently selected from F, Cl or a perfluoroalkyl group having 1 to 10 carbon atoms, a=0, 1 or 2, and b=0 to 6; with a carbanion derived from a methylene compound represented by the formula $CH_2YZ$ wherein Y and Z are electron-withdrawing groups selected from the group consisting of CN, $SO_2R_f$, $SO_2R^3$, $P(O)(OR^3)_2$, $CO_2R^3$, $P(O)R^3{}_2$, $C(O)R_fC(O)R^3$, and cycloalkenyl groups formed therewith, wherein $R_f$ is a perfluoroalkyl group of 1–10 carbons, optionally substituted with one or more ether oxygens, $R^3$ is an alkyl group of 1–6 carbons, optionally substituted with one or more ether oxygens or an aryl group optionally further substituted; and wherein Y and Z may be either the same or different to form a reaction mixture; reacting said mixture until the desired degree of conversion has been achieved; and, removing majority of said organic liquid.

The present invention further provides a process for forming an ionomer, the process comprising combining in an aqueous reaction medium VF2 with an ionic monomer represented by the formula

$$CF_2=CF\text{---}(OCF_2CFR)_aOCF_2(CFR')_bSO_2X^-(M^+)(Y)(Z)_c \quad (II)$$

wherein

R and R' are independently selected from F, Cl or a perfluoroalkyl group having 1 to 10 carbon atoms optionally substituted with one or more ether oxygens;

a=0, 1 or 2;

b=0 to 6;

$M^+$ is $H^+$ or a univalent metal cation;

X is C or N with the proviso that c=1 when X is C and c=0 when X is N;

when c=1, Y and Z are electron-withdrawing groups selected from the group consisting of CN, $SO_2R_f$, $SO_2R^3$, $P(O)(OR^3)_2$, $CO_2R^3$, $P(O)R^3{}_2$, $C(O)R_fC(O)R^3$, and cycloalkenyl groups formed therewith wherein $R_f$ is a perfluoroalkyl group of 1–10 carbons optionally substituted with one or more ether oxygens;

$R^3$ is methyl or ethyl;

Y and Z are the same or different;

or, when c=0, Y may be an electron-withdrawing group represented by the formula $-SO_2R_f'$ where $R_f'$ is the radical represented by the formula $-(R_f''SO_2N^-(M^+)SO_2)_mR_f'''$ where m=0 or 1, and $R_f''$ is $-C_nF_{2n}-$ and $R_f'''$ is $C_nF_{2n+1}$ where n=1–10, optionally substituted by one or more ether oxygens to form a reaction mixture;

introducing a free radical initiator;

reacting said reaction mixture to form an ionomer having a melting point of 150° C. or greater.

The present invention further provides for an ionically conductive composition comprising the polymer of the invention and a liquid imibibed therewithin.

The present invention further provides for an electrode comprising at least one electrode active material, the ionomeric polymer of the present invention mixed therewith, and a liquid imbibed therewithin.

The present invention further comprises an electrochemical cell comprising a positive electrode, a negative electrode, a separator disposed between the positive and negative electrodes, and a means for connecting the cell to an outside load or source wherein at least one of the group consisting of the separator, the cathode, and the anode, comprises the ionically conductive composition of the invention.

DETAILED DESCRIPTION OF THE INVENTION

For the purposes of the present invention, the term sulfonyl methide refers to a functional group wherein an ionically bonded carbon atom is also bonded to at least one fluoroalkylsulfonyl group, while the term sulfonyl imide refers to a functional group wherein an ionically bonded nitrogen atom is also bonded to at least one fluoroalkylsulfonyl group.

Surprisingly, the conductive compositions of the present invention are readily melt processable into electrodes and separators useful in assembling batteries in low cost continuous or semi-continuous manufacturing processes. No previous ionomer based composition suitable for use in electrochemical cells is known to exhibit melt processability.

The ionomers of the present invention comprise monomer units derived from VF2 and 0.5–50 mol-%, preferably 2–20 mol-%, most preferably 3–12 mol-%, of ionic monomer units having pendant groups comprising the radical represented by the formula

$$-(OCF_2CFR)_aOCF_2(CFR')_bSO_2X^-(M^+)(Y)(Z)_c$$

wherein

R and R' are independently selected from F, Cl or a perfluoroalkyl group having 1 to 10 carbon atoms optionally substitued by one or more ether oxygens;

$a=0$, 1 or 2;

$b=0$ to 6;

$M^+$ is $H^+$ or a univalent metal cation;

X is C or N with the proviso that $c=1$ when X is C and $c=0$ when X is N;

when $c=1$, Y and Z are electron-withdrawing groups selected from the group consisting of CN, $SO_2R_f$, $SO_2R^3$, $P(O)(OR^3)_2$, $CO_2R^3$, $P(O)R^3{}_2$, $C(O)R_fC(O)R^3$, and cycloalkenyl groups formed therewith wherein $R_f$ is a perfluoroalkyl group of 1–10 carbons optionally substituted with one or more ether oxygens;

$R^3$ is an alkyl group of 1–6 carbons optionally substituted with one or more ether oxygens, or an aryl group optionally further substituted;

Y and Z are the same or different;

or, when $c=0$, Y may be an electron-withdrawing group represented by the formula $-SO_2R_f'$ where $R_f'$ is the radical represented by the formula $-(R_f''SO_2N^-(M^+)SO_2)_m R_f'''$ where $m=0$ or 1, and $R_f''$ is $-C_nF_{2n}-$ and $R_f'''$ is $-C_nF_{2n+1}$ where $n=1-10$, optionally substituted by one or more ether oxygens.

Preferably, $a=0$ or 1, $R=CF_3$, $R'=F$, $b=1$, and when X is C, Y and Z are CN or $CO_2R^3$ where $R^3$ is $C_2H_5$, while when X is N, Y is preferably $SO_2R_f$ where $R_f$ is $CF_3$ or $C_2F_5$ and $M^+$ is $H^+$ or alkali metal cation. Most preferably $M^+$ is a lithium cation. Most preferably the ionomer of the invention exhibits a melting point of 150° C. or higher as determined by the peak of the endotherm as measured by differential scanning calorimetry (ASTMD4591).

The methide ionomers of the present invention may be formed by copolymerization of (II) with VF2 according to the teachings of Connolly, op.cit. Preferably, however, the methide ionomer is made by the process of the invention, wherein in a preparatory step is formed a copolymer of VF2 with the sulfonyl fluoride monomer (III).

The polymerization of (III) with VF2 may be conducted according to the teachings of Connolly et al, op. cit. Preferably, the polymerization is conducted with pre-emulsified liquid comonomer in a reaction mixture as taught hereinbelow. The ionomers formed from non-ionic polymer which has been polymerized in such fashion exhibit surprisingly high melting points of ca. 150° C. or higher as determined from the peak of the endotherm in differential scanning calorimetry (ASTM D4591) in view of their bulk comonomer contents.

In the process of making the methide ionomer, the non-ionic sulfonyl fluoride copolymer, however formed, is then contacted in an inert organic liquid at a temperature of 0–150° C., preferably 20–70° C., with a carbanion derived from $CH_2YZ$, wherein Y and Z are electron-withdrawing groups selected from the group consisting of CN, $SO_2R_f$, $SO_2R^3$, $P(O)(OR^3)_2$, $CO_2R^3$, $P(O)R^3{}_2$, $C(O)R_fC(O)R^3$, and cycloalkenyl groups formed therewith wherein $R_f$ is a perfluoroalkyl group of 1–10 carbons optionally substituted with one or more ether oxygens;

$R^3$ is an alkyl group of 1–6 carbons optionally substituted with one or more ether oxygens, or an aryl group optionally further substituted;

Y and Z are the same or different.

Preferably Y and Z are CN or $CO_2R^3$ where $R^3$ is $C_2H_5$, and the base used to generate reactive species from $CH_2YZ$ is preferably an alkali metal hydride, most preferably lithium hydride.

The combination is allowed to react until the sulfonyl fluoride is completely converted, which takes typically 15–20 hours in the preferred temperature range of 20–70° C.

Most preferably, $CH_2YZ$ as hereinabove described, is combined with the copolymer of VF2 and (III), and lithium hydride in the inert organic liquid in the ratio of one gram equivalent weight of $CH_2YZ$ and two gram equivalent weights of lithium hydride per gram equivalent weight of sulfonyl fluoride.

Suitable inert organic liquids include oxygen-containing solvents such as dialkyl ethers, dimethoxyethane, tetrahydrofuran, dioxane, sulfolane, dimethyl sulfoxide, n-methyl pyrrolidone, dimethyl formamide, and acetonitrile. The preferred solvent will also be readily removed upon completion of the reaction. Preferred is dimethoxyethane.

The metal fluoride coproduct formed in the methidization process of the invention may be removed, if desired, by extraction or a dialysis process using water.

It is found in the practice of the invention, that in the formation of ionomers, the liquid medium in which the ionic species is formed often forms highly stable solvates therewith, making it difficult to fully remove that liquid by ordinary means such as drying or distillation. The residual liquid is preferably removed by addition of another metal ion ligating agent such as an organic carbonate, sulfolane, alkylphosphate, or dimethoxyethane which replaces the residual liquid, typically at moderately elevated temperatures in an anhydrous fluid such as toluene.

A monomeric form of the methide moiety of the ionomer of the invention may be formed by starting with the unsaturated olefinic structure (III), followed by bromination as is known in the art in order to protect the double bond, reaction as hereinabove described for the analogous copolymer, followed by treatment with Zn powder to yield the polymerizable double bond.

To form the imide ionomer of the present invention, VF2 is copolymerized with the monomeric composition represented by $$CF_2=CF(OCF_2CFR)_aOCF_2(CFR')_bSO_2N(M^+)SO_2R_f' \qquad (V)$$

R and R' are independently selected from F, Cl or a perfluoroalkyl group having 1 to 10 carbon atoms optionally substituted by one or more ether oxygens;

$a=0$, 1 or 2;

$b=0$ to 6;

$M^+$ is $H^+$ or a univalent metal cation, $R_f'$ is the radical represented by the formula $-(R_f''SO_2N-(M^+)SO_2)_mR_f'''$ where $m=0$ or 1, and $R_f''$ is $-C_nF_{2n}-$ and $R_f'''$ is $-C_nF_{2n+1}$ where $n=1-10$, optionally substituted by one or more ether oxygens.

Preferably, $a=0$ or 1, $R=CF_3$, $R'=F$, $b=1$, and when X is $R_f$ is $CF_3$ or $C_2F_5$, and $M^+$ is an alkali metal cation, most preferably lithium cation.

The olefinic monomer (V) may be synthesized according to the teachings of Xue, op.cit. The polymerization may be effected according to the teachings of Connolly et al, op. cit.

It is found in the practice of the present invention that the method by which the ionomer is formed can have a large effect on the melting temperature of the ionomer formed thereby. Melting point is of importance because a higher melting ionomer will provide a higher use temperature in such applications as lithium batteries.

The prior art teaches an aqueous emulsion process for copolymerizing methide or imide monomers according to DesMarteau or Xue, op. cit, with tetrafluoroethylene (TFE). Reaction kinetics dictate that the process of DesMarteau necessarily will result in limited, nearly random incorporation of the imide or methide monomers. An alternative though less convenient process known in the art, is to polymerize in a perfluorinated solvent.

Because of very substantial differences in reaction kinetics, the rate of incorporation and distribution of a comonomer in copolymerization with VF2 depends upon the availability of the comonomer in the aqueous polymerization medium. It has been found very surprisingly than when the methide and imide ionomers herein are copolymerized with VF2 in the aqueous emulsion polymerization of the art such as in Connolly et al, op. cit., ionically rich and ionically poor regions are developed. This results in an ionomer exhibiting a melting temperature higher than that achieved when an ionomer of the same over-all composition is formed by first copolymerizing VF2 with (III) using the same process followed by forming the ionomer.

An alternative means for providing the desired higher melting ionomer while avoiding the pitfalls of unwanted side reactions associated with polymerizing the ionic species, is to copolymerize VF2 with (III) in an aqueous medium wherein the liquid-liquid interface is substantially increased over that in the method of Connolly such as that in which the water, surfactant and monomer are pre-emulsified under very high shear mixing conditions as hereinbelow described.

Alternative means for achieving the high melting ionomers of the invention are available by copolymerizing VF2 with (III) in perfluorinated solvents, but this is less preferred because of the expense and handling difficulties inherent therewith.

It is found in the practice of the invention that it is preferred to make the methide ionomer by polymerizing VF2 with (III) in a pre-emulsified state as hereinbelow described, followed by forming the methide as hereinabove described. However, the imide is preferably formed by first forming the imide monomer according to Xue, op. cit., followed by polymerizing in an aqueous medium along the lines of Connolly, op.cit. In both approaches, the preferred method results in the preferred ionomer having a melting point of 150° C. and above.

The imide analog of (II) may be synthesized by exposing a composition represented by the formula $$CF_2=CF(OCF_2CFR)_aOCF_2(CFR')_bSO_2F \qquad (III)$$

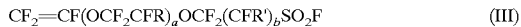

made according to the teachings of Asahi Chemical Industry, GB 2051 831, 1980 (K. Kimoto, H. Miyauchi, J. Ohmura, M. Ebisawa et al.) to bromine or chlorine in an anhydrous inert atmosphere at a temperature of ca. 0° C. in order to protect the olefinic bond according to the teaching in U.S. Pat. No. 5,463,005 forming thereby a composition represented by (IV). After washing to remove excess halogen using for example $NaHSO_3$, the thus brominated starting material is combined under dry conditions, preferably in an anhydrous, aprotic organic solvent, with anhydrous MF, where M is K or Cs, and a composition represented by the formula $R_f'SO_2NH_2$, where $R_f'$ is the radical represented by the formula $-(R_f'SO_2N-(M^+)SO_2)_mR_f'''$ where m=0 or 1, or possibly >1, and $R_f''$ is $C_nF_{2n}$ and $R_f'''$ is represented by the formula $C_nF_{2n+1}$ where n=1 to 10, $R_f'SO_2NH_2$ being made according to the teachings of Meußendoerffer and Niederprüm (Chemiker Zeitung, 96. Jahrgang (1972) No. 10, 583). Suitable solvents include acetonitrile, dioxane, and sulfolane.

Preferably $R_f'$ is $C_nF_{2n+1}$ where n=1 to 4.

The mixture thus formed is heated to a temperature in the range of 50–150° C., preferably 70–90° C., and the reaction is allowed to proceed preferably until the $R_f'SO_2NH_2$ has been consumed as determined by NMR. Upon termination of the reaction, the product, which remains in solution is separated by filtration. In order to regenerate the olefinic bond, the reaction product is then contacted with metallic zinc, preferably by slurrying Zn powder into the solution, at ambient temperature and then heated for several hours, as taught in U.S. Pat. No. 5,463,005, preferably followed by filtering and washing with an anhydrous, aprotic organic solvent such as acetonitrile. Thus formed is a composition represented by the formula:

$$CF_2=CF(OCF_2CFR)_aOCF_2(CFR')_bSO_2N(M)SO_2R_f' \qquad (V)$$

The lithiated imide form of structure (V) is then copolymerized with VF2 according to the teachings of Connolly et al. Unlike the methide embodiment, wherein it is preferred to first make a copolymer of VF2 and (II) followed by methidization, in the case of the imide it is highly preferred to first make the imidized monomer (V) followed by polymerization with VF2.

In many applications, the ionomer is preferably formed into a film or sheet. Films may be formed according to processes known in the art. In one embodiment, the ionomer is diluted with a solvent such as DMAC, the mixture cast onto a smooth surface such as a glass plate using a doctor knife or other device known in the art to assist in depositing films on a substrate, and the solvent evaporated. Preferably the ionomer of the invention is first combined with a plasticizer and then is formed into a film or sheet by a melt process. Most preferably, the melt process is an extrusion process.

The ionomers of the present invention, however formed, may exhibit a low level of ionic conductivity in the dry state, typically about $10^{-7}$ S/cm at room temperature. The ionomer may be combined with a liquid to achieve higher levels of ionic conductivity. Depending upon the requirements of the application, the ionomer will be in the acid form or the metal salt form, the particular metal being determined by the application as well. The liquid employed therewith will likewise be dictated by the application. In general terms, it has been found in the practice of the invention that conductivity of the liquid-containing ionomer increases with increasing percent weight uptake, increasing dielectric constant, and increasing Lewis basicity of the liquid, while conductivity has been observed to decrease with increasing viscosity and increasing molecular size of the liquid employed. Thus, a highly basic solvent of low viscosity and small molecular size but low dielectric constant may provide superior conductivity in a given membrane than a larger, more viscous, less basic solvent of very high dielectric constant. Of course, other considerations may come into play as well. For example, the liquid may be electrochemically unstable in the intended use.

Conductive compositions may thus be formed by combining together the ionomers of the present invention with solvents using a variety of techniques known in the art such as imbibing a dry ionomer film in a mixture of solvents or exposure of a dry film to a solvent vapor under controlled conditions or combining the ionomer with the solvents in a melt state and extruding films of controlled composition. Preferred solvents include water, nonaqueous solvents such as linear and cyclic carbonates, alcohols, esters, lactones, ethers, sulfoxides, amides, sulfonamides, and sulfones, subject to the general considerations discussed above. The solvents combined with the ionomers of the present invention to form conductive compositions can optionally contain additional mobile salts which may be preferred for specific applications. Other solvents suitable for forming conductive compositions include ionic liquids such as 1-methyl-3-butyl-imidazolium trifluoromethane sulfonate.

A variety of chemical agents can be added to these conductive compositions for purposes of improving ionic conductivity through the influence of the chemical agent on the dissociation or mobility of the ions within the ionomeric polymer. Such chemical agents include but are not limited to cationic complexing agents such as crown ethers and aza ethers and anion complexing agents such as $BR_3$ compounds where R is aryl, fluoro-substituted alkyl or aryl.

The ionomers of the present invention provide several unexpected benefits over the ionomers of the art. It is known in the art that VF2 polymers and copolymers exhibit electrochemical stability which makes them structural materials of choice for use in lithium batteries. Compared to the ionomers in the art which contain fluorosulfonate salts, the ionomers of the present invention comprise fluorosulfonyl-methide or imide salts which exhibit higher dissociation in organic solvents thereby providing conductive compositions formed therefrom with surprisingly high conductivity. The preferred conductive compositions of the present invention, comprising the lithium salt embodiments of the ionomers of the invention and aprotic organic solvents, most preferably organic carbonates and lactones, are particularly well-suited for use in lithium batteries.

In an additive effect thereto, it is found, surprisingly, that the ionomers of the present invention exhibit particularly high affinity and phase compatibility with organic solvents as compared to the ionomers of DesMarteau, op. cit., formed with TFE. The higher affinity of the ionomers of the invention to organic solvents on the one hand makes melt processing or casting of membranes a useful process for the production thereof; and, on the other hand, provides for higher uptake of the preferred organic carbonates in the preferred conductive compositions of the invention, leading to higher conductivities thereby.

It is found in the practice of the invention that certain compositions of an ionomer of the invention containing at least 50% VF2 more preferably at least 80% VF2 may become plasticized by the solvents imbibed within it, with concomitant decrease in mechanical strength of the membrane. In some applications, it may be desirable to enhance the properties of the solvent-swollen membrane. Means available for improving the mechanical properties include: 1) incorporation into the polymer by means known in the art, a non-ionic third monomer that is not solvent sensitive; 2) formation by known means of a polymer blend with a non-ionic polymer that is less solvent sensitive; 3) blending by known means of the ionomer of the invention with an inert filler; 4) blending different compositions of ionic copolymers.

In a preferred embodiment of this invention involves the use of compositionally heterogeneous —$SO_2F$— containing copolymer as precursor for the ionomeric form. Combined attributes of increased conductivity and enhanced mechanical strength are thereby obtained.

Suitable third monomers which may be usefully incorporated in these ionomeric compositions include tetrafluoroethylene, chlorotrifluoroethylene, ethylene, hexafluoropropylene, trifluoroethylene, vinyl fluoride, vinyl chloride, vinylidene chloride, perfluoroalkylvinyl ethers of the formula $CF_2=CFOR_f$ where $R_f=CF_3$, $C_2F_5$ or $C_3F_7$. Preferred termonomers include tetrafluoroethylene, hexafluoropropylene, ethylene and the perfluoroalkylvinyl ethers. Termonomers are preferably present in the polymer at a concentration of up to 30 mol-%.

Polymers suitable for blending with ionomers of the invention include poly(tetrafluoroethylene) and copolymers thereof with hexafluoropropylene or perfluoroalkyl vinyl ethers, polyvinylidene fluoride homopolymer and a copolymer thereof with hexafluoropropylene, and polyethylene oxide. A preferred composition comprises 25 to 50 weight % PVF2 homopolymer blended with the VF2 ionomer of the present invention. These materials are blended together by means common in the art such as mixing in a common diluent such as DMAC or propylene carbonate and then casting a membrane.

Suitable inert fillers include $SiO_2$, $Al_2O_3$, $TiO_2$, or $CaF_2$. High surface area particles less than 1.0 micron in diameter are desired, such as are available for the preferred grade of $SiO_2$ under the trade name Cab-o-sil® TS-530 silica. Loadings of up to 50 weight % filler are preferred.

The preferred electrode of the invention comprises a mixture of one or more electrode active materials in particulate form, the ionomer of the invention, at least one electron conductive additive, and at least one organic carbonate. Examples of useful anode active materials include, but are not limited to, carbon (graphitic, coke-type, mesocarbon microbeads, carbon fibers, polyacenes, and the like) and lithium-intercalated carbon, lithium metal nitrides such as $Li_{2.6}Co_{0.4}N$, lithium metal, and lithium alloys, such as alloys of lithium with aluminum, tin, magnesium, mercury, manganese, iron, antimony, cadmium, and zinc, alloy forming anode compounds with inert metallic frameworks such as tin-iron-carbon or tin-manganese-carbon ternary compounds, metal oxides or lithium metal oxides such as tin oxide, iron oxide, titanium oxide, tantalum oxide, niobium oxide, or tungsten oxide, and electronically anion or cation-doping conductive polymers such as polyaniline. Lithium intercalation anodes employing graphitic carbon such as MCMB 2528 from Osaka Gas Chemical Co. are preferred.

Useful cathode active materials include, but are not limited to, transition metal oxides such as spinel $LiMn_2O_4$, layered $LiMnO_2$, $LiNiO_2$, $LiCoO_2$, $LiNi_xCo_yO_2$, iron oxides or lithiated iron oxides such as $LiFeO_2$, or vanadium oxides such as $LiV_2O_5$, $LiV_6O_{13}$, $LiNiVO_4$, $LiCoVO_4$, or the above compounds in nonstoichiometric, disordered, amorphous, or overlithiated or underlithiated forms (such as having metallic vacancies, oxygen vacancies or defects, etc.), the above compounds doped with small amounts of other divalent or trivalent metallic cations such as $Fe^{2+}$, $Ti^{2+}$, $Zn^{2+}$, $Ni^{2+}$, $Co^{2+}$, $Cu^{2+}$, $Cr^{3+}$, $Fe^{3+}$, $Al^{3+}$, $Ni^{3+}$, $Co^{3+}$, $Mn^{3+}$, etc., sulfur compounds such as solid sulfur, organic disulfides, or metal sulfides such as $TiS_2$ or $MoS_2$, electronically-conducting polymers such as polyaniline and its derivatives, polypyrrole derivatives, polyparaphenylene derivatives, polythiophene derivatives, or their copolymers, or mixtures of any of the above compounds. Particle size of the active material should range from about 1 to 100 microns. Preferred are transition metal oxides such as $LiMn_2O_4$, $LiNiO_2$, $LiCoO_2$, and $LiNi_xCo_yO_2$. A highly preferred electron conductive aid is carbon black, preferably Super P carbon black, available from the MMM S.A. Carbon, Brussels, Belgium, in the concentration range of 1–10%. Preferably, the volume fraction of the lithium ionomer in the finished electrode is between 4 and 40%.

The electrode of the invention may conveniently be made by dispersion or dissolution of all polymeric components into a common solvent and mixing together with the electrode active particles the carbon black particles. For cathodes the preferred electrode active material is $LiNi_xCo_{1-x}O_2$ wherein $0<x<1$, while for anodes the preferred electrode active material is graphitized mesocarbon microbeads. For example, a preferred lithium battery electrode of the invention can be fabricated by dispersing or dissolving ionomer of the invention in a mixture of propylene carbonate and cyclopentanone, followed by addition of particles of electrode active material and carbon black, followed by deposition of a film on a substrate and drying. Preferably, the components of the electrode are mixed together and fed to an extruder wherein they are mixed to form a homogeneous melt and extruded into a film.

The resultant preferred electrode will comprise electrode active material, conductive carbon black, and ionomer of the invention, where, preferably, the weight ratio of ionomer to electrode active material is between 0.05 and 0.8 and the weight ratio of carbon black to electrode active material is between 0.01 and 0.2. Most preferably the weight ratio of ionomer to electrode active material is between 0.1 and 0.25 and the weight ratio of carbon black to electrode active material is between 0.02 and 0.1. This electrode can then be cast from solution onto a suitable support such as a glass plate, inert polymer carrier web, or current collector metal foil, and formed into a film using techniques well-known in the art. The electrode film thus produced can then be incorporated into a multi-layer electrochemical cell structure by lamination.

Battery solvents may be added to the battery component films individually or added to the battery laminated cells using a variety of techniques known in the art such as imbibing by immersion into a solution or exposure to solvent vapors under controlled conditions. Preferred battery solvents for forming conductive compositions with the ionomeric polymers of the present invention suitable for usage in lithium batteries include dipolar aprotic liquids such as the linear and cyclic carbonates, esters, lactones, amides, sulfoxides, sulfones, sulfamides, and ethers. Preferred solvents are mixtures of cyclic carbonates or lactones such as ethylene carbonate, propylene carbonate, butylene carbonates, vinylene carbonate, gamma-butyrolactone, fluoro or chloro-substituted cyclic carbonates with linear carbonates such as dimethyl carbonate, diethyl carbonate, dipropyl carbonate, ethyl methyl carbonate, methyl propyl carbonate, and fluoro and chloro substituted linear carbonates. Especially preferred are mixtures of ethylene carbonate, propylene carbonate, and gamma-butyrolactone with linear carbonates such as diethyl carbonate and/or ethyl methyl carbonate. Most preferred are mixtures of ethylene carbonate with propylene carbonate in weight ratios of from 50:50 to 80:20 of ethylene carbonate to propylene carbonate.

These solvents can optionally be combined with additional mobile salts such as the lithium salts $LiPF_6$, $LiPF_xRf_y$ where $Rf=CF_3$, $CF_2CF_3$, or other perfluorinated electron-withdrawing groups, $LiBF_4$, $LiAsF_6$, $LiClO_4$, $LiSO_3Rf$ where $Rf=CF_3$, $CF_2CF_3$, or other perfluorinated electron-withdrawing groups, $LiN(SO_2R1)(SO_2R2)$ where R1 and $R2=CF_3$, $CF_2CF_3$, or other electron-withdrawing groups and R1 is not necessarily the same as R2, $LiC(SO_2R3)(SO_2R4)(SO_2R5)$ where R3, R4, and $R5=CF_3$, $CF_2CF_3$, or other electron-withdrawing groups and R3, R4 and R5 are not necessarily the same and mixtures of the above salts. Preferred are $LiPF_6$ or $LiN(SO_2CF_2CF_3)_2$.

In a preferred embodiment of the battery of the present invention, a battery is formed from one or more electrochemical cells formed by laminating together in film form the anode, cathode, and separator compositions of the present invention, all of which have been rigorously dried prior to addition of a liquid selected from the group of organic carbonates and mixtures thereof, a mixture of ethylene carbonate and propylene carbonate being most preferred.

In a more preferred embodiment of the battery of the present invention, the individual film layers consisting of an anode, separator, and cathode are compounded individually in a melt state and extruded into film form using temperatures from 90 to 130° C. These individual layers already containing the preferred battery solvents such as mixtures of ethylene carbonate and propylene carbonate are laminated together to form battery cells which do not require additional post-treatment such as drying or extraction steps.

It may be desirable to incorporate into the electrode composition of the invention additional polymers or solvents for such purposes as improving the binding of the components thereof, or providing improved structural integrity of an article fabricated therefrom. One particularly preferred additional material is PVF2 homopolymer, which may be incorporated simply by dissolving the polymer into the same solution from which the electrode is being formed or melt compounding the polymer into other components during mixing or extrusion, as hereinabove described.

EXAMPLES

Example 1

The sulfonimide $CF_2=CFOCF_2CF(CF_3)OCF_2CF_2SO_2NHSO_2CF_3$ is prepared as described by DesMarteau (U.S. Pat. No. 5,463,005 (1995) and Xue (Ph.D. thesis (1996), Clemson University, Clemson), and is converted to its lithium salt by stirring in aqueous solution with 1 equivalent of lithium hydroxide at room temperature. After evaporating the water, the dried lithium salt (29.1 g, 0.05 mole) in 500 ml of deionized water is charged to a 1-liter vertical stirred autoclave. The vessel is closed, twice pressured to 100 psi nitrogen and vented, cooled to about 5° C. and evacuated. Vinylidene fluoride (50.0 g, 0.78 mol) is added, and the stirred (750 rpm) contents are heated to 60° C. A solution of potassium persulfate (0.08 g in 20 mL water) is added over a 10 minute interval. After about 8 hours, the remaining pressure is vented and the aqueous solution is evaporated to dryness giving a copolymer containing $CH_2CF_2$ and $CF_2CF(OCF_2CF(CF_3)OCF_2CF_2SO_2NLiSO_2CF_3)$ units as a white solid identified by its fluorine NMR spectrum.

Example 2

The sulfonyl fluoride $CF_2ClCFClOCF_2CF(CF_3)OCF_2CF_2SO_2F$, prepared as described by DesMarteau, U.S. Pat. No. 5,463,005 (1995) is converted to the lithium methide salt $CF_2ClCFClOCF_2CF(CF_3)OCF_2CF_2SO_2C(Li)(SO_2CF_3)_2$ by the procedure described by Waddell et al. in Example 4 of U.S. Pat. No. 5,514,493 (1996). Treatment of this compound with zinc dust in acetic anhydride at 80–90° C. affords the olefinic methide monomer $CF_2=CFOCF_2CF(CF_3)OCF_2CF_2SO_2C(Li)(SO_2CF_3)_2$. This monomer (35.6 g, 0.05 mole) in 500 ml of deionized water is charged to a 1-liter vertical stirred autoclave. The vessel is closed, twice pressured to 100 psi nitrogen and vented, cooled to about 5° C. and evacuated. Vinylidene fluoride (50.0 g, 0.78 mol) is added, and the stirred (750 rpm) contents are heated to 60° C. A solution of potassium persulfate (0.08 g in 20 mL water) is added over a 10 minute interval. After about 8 hours, the remaining pressure is vented and the aqueous solution is evaporated to dryness giving a copolymer containing $CH_2CF_2$ and $CF_2CF(OCF_2CF(CF_3)OCF_2CF_2SO_2C(Li)(SO_2CF_3)_2)$ units as a white solid identified by its fluorine NMR spectrum.

Example 3

A copolymer of VF2 and PSEPVE was synthesized according to the following method. 150 g of PSEPVE liquid was suspended in aqueous emulsion by combining with a solution of 35 g of ammonium perfluorooctanoate in 600 ml of distilled water using a Microfluidics, Inc. microfluidizer. The suspension was then diluted to 1 liter total volume with additional distilled water. The suspension so formed was charged to a nitrogen purged 4 liter horizontal autoclave equipped with a mechanical agitator, along with an additional 1500 mL of distilled water. The reactor was evacuated, then pressurized to 0 psig with vinylidene fluoride three times, then heated to 60° C., pressurized to 300 psig with vinylidene fluoride, and agitated at 200 rpm. A solution of aqueous potassium persulfate (0.6%, 50 mL) was added over a 5 min period. Reactor pressure was maintained at 300 psi until 220 g of VF2 had been fed after initiator addition. Agitation was stopped and the reactor was cooled and vented. The resulting milky dispersion was frozen and thawed to coagulate the product which was filtered through Nylon cloth and washed with water repeatedly to remove surfactant. After air drying, polymer crumb was dried in a nitrogen-purged vacuum oven at 100° C. for 24 hr to give 364 g of product. $^{19}$F NMR data (acetone): +45.2 (s,), −78.0 to −80.0 (m's), −90.0 to −95 (m's), −108 to −116 (series of m), −122.0 to −127.5 (m's), −143.0 (bd s), consistent with mol % PSEPVE=9.5%. TGA (10°/min, N$_2$): no weight loss until 375° C. DSC (20°/min): maximum of broad melting transition at 162° C. (23 J/g); Tg=−20° C.

A 100 mL flask was charged with malonontrile (0.63 g, 9.5 mmol) and dimethoxyethane (10 mL). Sodium hydride (0.228 g, 9.5 mmol) was added in portions. The mixture was stirred at room temperature for ca. 15 min until gas evolution was complete. 5 g of the VF2/PSEPVE copolymer, corresponding to 4.73 mequiv. of SO2F, was suspended in dimethoxyethane (50 mL), treated in one portion with the above malononitrile anion solution. The mixture was stirred for 18 hr at which time $^{19}$F NMR spectral analysis showed essentially complete conversion of SO2F groups to SO2C (CN)2 groups: −78.0 to −82.0 (m, distinctly different lineshape vs. SO3 form, a=7.00), −92.0 to −96.6 with major intensity singlet at −92.7, minor at −93.1 and −96.6 (combined a=16.868), −109 to −113 (m) and "defect" VF2 peaks at −115.0 and −117.3, CF2SO2-at −117.9 (combined a=5.206), −123 to −128 (bd m, a=1.543), −145.8 (m, a=1.011). Integration is consistent with 9.8 mol% Na-dicyanomethide form of functional comonomer. The reaction mixture was treated with dry toluene (50 mL) and filtered to provide 5.70 g red-pink solid after removal of residual solvent at high vacuum. $^1$H NMR (acetone-d6) was in accord with one dimethoxyethane molecule/polymer-bound sodium ion.

Sodium ions were exchanged for lithium ions using the following procedure. A 4.0 g sample of the sodium form of the copolymer was suspended in 100 mL water containing 4.5 g LiCl and stirred for 1 hr. The aqueous layer was decanted, then replaced with another aqueous LiCl solution further modified by addition of methanol (40 mL). After 18 hr, the top phase was decanted and replaced with another aqueous charge of LiCl, and the mixture was stirred and filtered. The solid was washed with distilled water until chloride ion in the effluent could not be detected. The red solid was air dried, then azeotropically dried using toluene. Ethylene carbonate (0.44 g, 5 mmol; dissolved in toluene (5 mL) was added to the copolymer suspension in toluene, and distillation was continued until water was no longer evident in the distillate. The resulting solid was collected by filtration under nitrogen, then placed on a high vacuum line for 3 hr. to provide 4.0 g of solid. IR (thin film) exhibited band at 2205 cm−1 assigned to CN stretch.

1H NMR was consistent with one ethylene carbonate molecule/polymer-bound Li ion. ICP showed that exchange of Li for Na was essentially complete. DSC: peak melting temperature=160.6° (15.8 J/g).

Example 4

In the present example, a small molecule reaction is presented as an analog to the formation of a cyano-substituted methide ionomer. A mixture of dimethoxyethane (30 mL), nonafluorobutane sulfonyl fluoride (1.43 g, 4.75 mmol), and sodium hydride (0.228 g, 9.5 mmol) was treated slowly with a solution of malononitrile (0.314 g, 4.75 mmol) in dimethoxyethane (4 mL). Temperature increased to 35° C. with evolution of gas. The mixture was stirred for 18 hr., filtered through glass fiber paper, and evaporated to provide 1.63 g of yellow solid. Crude product was recrystallized by dissolution in a minimal volume of tetrahydrofuran and adding diethyl ether to form solid. Mixture was cooled at −25° and filtered to afford 0.59 g of solid. IR: intense bands at 2219 cm$^{-1}$ and 2195 cm$^{-1}$ assigned to CN stretching bands. $^{19}$F NMR (THF-d8): −80.93 (m, a=27.3), −113.6 (m, a=17.6), −120.7 (m, a=18.8), −125.8 (m, a=18.7), consistent with CF$_3$CF$_2$CF$_2$CF$_2$SO$_2$C(CN)$_2$Na.

Example 5

In the present example, VF2/PSEPVE copolymer is converted to the lithium dicyanomethide derivative. A 300 mL flask was charged with VF2/PSEPVE copolymer (5.00 g, 4.73 mequiv. of SO$_2$F) and dimethoxyethane (100 mL). Lithium hydride (0.075 g, 9.5 mequiv) was added and the mixture was stirred while malononitrile (0.313 g, 4.75 mmol) was added as a solution in dimethoxyethane (5 mL). $^{19}$F NMR (DMSO-d6) spectrum was identical with that described in Example 3 and was consistent with complete conversion of SO$_2$F groups.

Bulk sample was allowed to settle and the supernatant removed. Dry toluene (100 mL) was added and the solid was collected by filtration. Removal of residual solvent under high vacuum afforded 5.54 g of red solid. $^1$H NMR (DMSO-d6): dimethoxyethane signals at 3.45 and 3.25, VF2 signal 3.15 to 2.7 and 2.4 to 2.18. DSC: peak melting temperature= 163.3° C. (14.5 J/g).

Example 6

1.0 gram of the lithium-form polymer of Example 3 was mixed with 2.5 grams of propylene carbonate (PC, E.M. Industries, Selectipur) on a hot plate at 100° C. in a nitrogen-purged Vacuum Atmospheres glove box until a clear deep red gel resulted. This gel was melt pressed at 120° C. with 3 klbs pressure using a Carver Hydraulic Unit Model #3912 press inside the glove box to give a 4.0 mil thick clear pink film. A 1.0 by 1.5 cm$^2$ section of this film was cut with a razor and assembled into a four-point-probe conductivity cell. Ionic conductivity was determined according to the method of Doyle et al, WO98/20573. The conductivity of the film under ambient conditions was equal to 7.75×10$^{-4}$ S/cm.

A second sample of this membrane was immersed into an excess of a 1:1 by volume mixture of ethylene carbonate (EC, E.M. Industries, Selectipur) and gamma-butyrolactone (GBL, E.M. Industries, Selectipur) for 30 minutes at room temperature. At the end of this period, the membrane sample was removed and blotted dry and its weight and ionic conductivity were measured. The film was highly swollen but still strong and elastic when fully imbibed with solvent. Weight uptake of the film was 766% and the ionic conductivity was 1.67×10$^{-3}$ S/cm.

A third sample of this membrane was immersed into an excess of a 1.0 M solution of LiPF6 (E.M. Industries) in 1:1 by volume EC/GBL for 30 minutes. At the end of this period, the membrane sample was removed and blotted dry and its weight and ionic conductivity were measured. The film had gained little total weight as a result of the imbibing period and its conductivity was $3.14 \times 10^{-3}$ S/cm.

Examples 7–16

In these examples, the following reagents were employed. Acetonitrile, purchased from EM Science (Gibbstown, N.J.) was refluxed over $P_2O_5$ for at least 12 h, collected under dry nitrogen; it was stored over activated 4 Å molecular sieves and used only in a dry box. Potassium fluoride was purchased from Aldrich Chemical Company; melted in a Pt dish with a torch and placed immediately in the chamber of the dry box; ground and stored thereafter inside the dry box. $CF_3SO_2NH_2$, purchased from TCI America (Portland, Oreg.), was sublimed twice at $10^{-3}$ Torr while using an oil bath temperature of 60° C. and a water cooled sublimation finger. Zn dust was purchased from Aldrich (<10 microns, 98+%) and activated with HCl according to standard procedures.

PSEPVE was synthesized according to the teachings of U.S. Pat. No. 5,463,005 (1995). It was distilled under vacuum. $I(CF_2)_4I$, available from TCI, Portland, Oreg., was converted to $NaSO_2(CF_2)_4SO_2Na$ followed by the reaction with chlorine to obtain $ClSO_2(CF_2)_4SO_2Cl$ according to the teachings of Qiu and Burton (J. Fluorine Chem., 60 (1993) 93–100). $C_4F_9I$, available from TCI, was converted to, $C_4F_9SO_2Cl$ according to the teachings of Hu and DesMarteau (Inorg.Chem. 32 (1993) 5007.

Example 7

248.0 g (0.556 mol) of distilled PSEPVE were cooled to 0° C. with an ice bath. Under a nitrogen atmosphere, 30 ml (0.582 mol) $Br_2$ were added dropwise with an addition funnel over a period of 6 h. The orange color of excess bromine persisted for 30 min. The reaction mixture was washed with 100 ml of a 5% NaHSO3 solution. The product turned milky. After washing with 100 ml water twice, the clear product was dried with $Na_2SO_4$ over night. The drying reagent was removed by filtration through a glass frit. The colorless, clear liquid was distilled at 40–45° C. at $10^{-3}$ Torr. 1.5 g of $P_2O_5$ were added and the compound underwent a second vacuum distillation at 40–45° C. at $10^{-3}$ Torr. Yield was 312.1 g.

Inside a dry-box filled with nitrogen, 15.4 g (104 mmol) of $CF_3SO_2NH_2$ obtained from TCI, Inc.(Portland, Oreg.) were placed in a 500 ml round bottom flask. 200 ml of anhydrous acetonitrile were added followed by 29.6 g (509.7 mmol) of anhydrous KF. 69.43 g (114.6 mmol) of the dried brominated PSEPVE prepared as hereinabove described were added. The reaction mixture was stirred and slowly heated to moderate reflux for 40 h. The reaction mixture was filtered through a paper filter inside the dry box. All volatiles were removed and the white residue was dried at 1 15° C. for 12 h under vacuum to provide 70.9 g of product.

The material was dissolved in 100 ml anhydrous DMF. 7.05 g (108 mmol) of Zn-powder were added to the filtrate and the mixture was stirred for 1 h at room temperature. The mixture was filtered and the residue was washed with additional 25 ml of anhydrous DMF.

The flask was brought outside the dry-box and most of the volatiles were removed under vacuum. The residue was heated under vacuum for 16 h at 115° C. The material contained traces of DMF. $^{19}$F-NMR in $CD_3CN$ showed the product was $CF_2$=$CFOCF_2CF(CF_3)OCF_2CF_2SO_2N(K)SO_2CF_3$ (8F, −77.8 −−79.3 ppm; 2F, −83.7 ppm; 1F, −112.65 ppm; 2F, −116.0 ppm; 1F, −121.0 ppm; 1F, −135.7 ppm; 1F, −144.2 ppm)

Example 8

150 ml of HCl conc. and 150 ml of deionized water were added to the product of Example 7, forming a brown, oily mixture which was stirred for 5 min and then four times extracted with fresh 100 ml aliquots of diethyl ether. The diethyl ether fractions were combined and washed three times with fresh 100 ml aliquots of deionized water. The ether was evaporated under vacuum and the remaining brown oil was transferred to a 100 ml round bottom flask. The brown, crude material underwent two shortpath distillations to obtain 50.6 g of the acid product $CF_2$=$CFOCF_2CF(CF_3)OCF_2CF_2SO_2N(H)SO_2CF_3$.

Example 9

34.08 g (59.26 mmol) of an acid product synthesized as in Example 8 was dissolved in 25 ml deionized water. 121.1 ml of a 0.489N LiOH solution was added. All water was removed under vacuum and the residue was dried at 100° C. for 24 h. Yield was 34.09 g of $CF_2$=$CFOCF_2CF$ $(CF_3)$ $OCF_2CF_2SO_2N(Li)SO_2CF_3$ 19F-NMR in $D_2O$: (8F, −77.8−−79.5 ppm; 2F, −86.0 ppm; 1F, −115.5 ppm; 2F, −117.3 ppm; 1F, −123.4 ppm; 1F, −137.7 ppm; 1F, −146.1 ppm); elemental analysis: N (2.45% found, 2.41% theor.), F (49.43% found, 52.31% theor.), Li (1.15% found, 1.19% theor.), S (10.83% found, 11.03% theor.).

Example 10

30.0 g (94.2 mmol) of $C_4F_9SO_2Cl$ were placed in a 250 ml round bottom flask. 125 ml of anhydrous acetonitrile and 55.1 g (948 mmol) of fused KF was added. The reaction mixture was stirred at room temperature for 42 h. All volatiles were removed and the residue was heated at 80° C. for 18h. 78.6 g (4.62 mol) anhydrous ammonia was added to the collected volatile fraction at −196° C. The reaction mixture was warmed to room temperature under an inert argon atmosphere allowing excess ammonia to evaporate overnight. All volatiles were removed under vacuum. The residue was heated to 45° C. for 5h under vacuum.

The residue was then treated with 150 ml anhydrous acetonitrile and filtered through a paper filter inside the dry-box, and solid was washed with an additional 100 ml of anhydrous acetonitrile. The solvent was removed under vacuum and the residue was sublimed (70° C., $10^{-3}$ Torr) to yield 19.38 g.

Inside the dry box, 32.9 g (54.3 mmol) of bromine protected PSEPVE prepared as in Example 7 was dissolved in 250 ml of anhydrous acetonitrile, 14.8 g (49.5 mmol) of the $C_4F_9SO_2NH_2$ prepared as hereinabove described were added, followed by the addition of 15.92 g (274 mmol) of fused KF. The reaction mixture was maintained at 80° C. for 96 h. The reaction mixture was cooled to room temperature and filtered. 5.45 g (83.3 mmol) Zn powder was added to the filtrate and the reaction mixture was stirred at room temperature for 45 min. The reaction mixture was heated to 60° C. for 15 h. The excess Zn and $ZnBr_2$ were removed by filtration and the solvent was removed under vacuum. The yellow residue was treated with 150 mL 6N HCl and the product was extracted with four portions of 150 ml ether. The combined organic layer was washed with 100 ml water, and the solvent was evaporated to yield, after shortpath distillation, 22.3 g of $CF_2=CFOCF_2CF(CF_3)OCF_2CF_2SO_2N(H)SO_2C_4F_9$, as confirmed by $^{19}F$ NMR.

Example 11

Inside a dry box, 200 ml of anhydrous acetonitrile was added to $ClSO_2(CF_2)_4SO_2Cl$ (23.1 g, 57.9 mmol) together with anhydrous KF (28.1 g, 484 mmol). The mixture was stirred at room temperature. Fluorine NMR showed that formation of the disulfonyl fluoride was complete after 17 h. The reaction flask, maintained under inert atmosphere, was equipped with a reflux and an addition funnel. The mixture was heated to 80° C. and treated with 5.81 g (100 mmol) of KF. 4.33 g (29.1 mmol) of $CF_3SO_2NH_2$ dissolved in 45 ml of anhydrous acetonitrile was added to the stirred suspension from the addition funnel over a period of 6.5 hours. The reaction mixture was stirred and heated for a total of 71 h. The reaction mixture was filtered, and the residue was washed with anhydrous acetonitrile. Combined filtrate was evaporated under vacuum and the beige residue was heated at 90° C. for 18 hr. Yield was 14.95 g of $CF_3SO_2N(K)SO_2(CF_2)_4SO_2F$ as confirmed by $^{19}F$ NMR in CD3CN: 44.9 ppm (SO2F, s, 1F), −80.6 ppm (CF3SO2, s, 3F), −108.2 ppm (CF2SO2, s, 2F), −114.2 ppm (CF2SO2, s, 2F), −120.7 ppm (CF2CF2SO2, s, 4F).

About 55 g of anhydrous ammonia were condensed to 14.95 g (28.1 mmol) of $CF_3SO_2N(K)SO_2(CF_2)_4SO_2F$ so prepared. The pressure in the flask was brought to 1 atm with argon and the reaction mixture was allowed to warm up to room temperature over a period of 5 h. The excess ammonia was allowed to escape. The beige residue was dried under vacuum and heated to 60° C. for 18 hr. Inside the dry-box, the product was dissolved in 150 ml of anhydrous acetonitrile and filtered. All volatiles were removed from the filtrate under vacuum to provide 12.7 g of product $CF_3SO_2N(K)SO_2(CF_2)_4SO_2NH_2$ which was dried at 90° C. for 12 hours.

Inside a dry-box, 20.2 g (33.3 mmol) of bromine-protected PSEPVE prepared as in Example 7 were added together with 125 ml of anhydrous acetonitrile to 12.7 g (24.0 mmol) of $CF_3SO_2N(K)SO_2(CF_2)_4SO_2NH_2$ prepared as hereinabove described. The reaction was started by the addition of 7.02 g (121 mmol) of fused KF. The reaction mixture was heated to 80° C. for 76 h. The reaction mixture was filtered through a paper filter to give the product $CF_3SO_2N(K)SO_2(CF_2)_4SO_2N(K)SO_2CF_2CF_2OCF(CF_3)CF_2OCFBrCF_2Br$. The product can readily be debrominated as in Example 7.

Example 12

According to the method of Example 1, a 1 liter autoclave was charged with a solution of 12.8 g (22.0 mmol) of the ionic lithium composition of Example 9 in 400 g deionized water. The solution was cooled and degassed and the reactor was charged with 15 g (0.234 mol) of vinylidene fluoride. The solution was brought to 60° C. (pressure in reactor: 116.1 psig; rpm: 750) after which 20 ml of a solution of 0.201 g potassium persulfate in 50 g deionized water was added over a period of 10 min. The reactor pressure diminished to 0 psig after 16 h. The copolymer was isolated by lyophilization. Yield was 24.9 g of copolymer characterized by 10.8 mol-% PSEPVE imide content, as shown by $^{19}F$ NMR. DSC showed $T_m$=163° C. ($2^{nd}$ heat). Elemental analysis: H (1.96% found, 1.49% theor.), N (1.25% found, 1.26% theor.), F (51.04% found, 55.68% theor.), S (5.40% found, 5.78% theor.)

$^1H$ NMR (acetone-d6): $CH_2$ at 3.85 ppm $^{19}F$ NMR (acetone-d6): −77.2—−79.2 ppm (m), −91.2—−130.0 ppm (series of m); −144.6 (1F, sidechain CF).

Example 13

0.865 g of the ionomer of Example 12 and 70 ml acetone was stirred for 12 h at room temperature and then poured into a 10 cm PFA dish. The solvent was allowed to evaporate slowly to provide a copolymer film which was peeled from the dish. The membrane was heated in a vacuum oven at 100° C. for 12 hours after which it became somewhat brittle. Film thickness was 120 micrometers.

Example 14

The procedure of Example 12 was followed, except the ionic comonomer used was 12.801 g of $CF_2=CFOCF_2CF(CF_3)OCF_2CF_2SO_2N(Li)SO_2CF_3$ (from Example 9) and the quantity of vinylidene fluoride was 29 g. The VF2-copolymer was isolated by lyophilization. The material was dried at 110° C. for 22 hr to afford the yield was 40.7 g of ionomer containing 4.7 mol-% of the lithium imide as confirmed by $^{19}F$ NMR. DSC ($2^{nd}$ heat) showed $T_m$−164.5° C. Elemental analysis: H (2.06% found, 2.16% theor.), N (1.78% found, 0.74% theor.), Li (0.32% found, 0.37% theor.). $^1H$ NMR (acetone-d6): $CH_2$ at 3.60 ppm. $^{19}F$ NMR (acetone-d6): −77.2—−79.2 ppm (m), −91.2—−130.0 ppm (series of m), −144.6 (sidechain CF).

Example 15

1.122 g of the ionomer of Example 14 were dissolved in 70 ml acetone and heated to reflux for 12 h. After the solution was cooled to room temperature, it was poured into a PFA dish and the solvent was allowed to evaporate slowly. A clear film was easily peeled from the PFA dish and was dried in a vacuum oven at 100° C. for 12 h. Thickness was 190 micrometers.

Example 16

A 100 mL flask is charged with 4.73 mmol of the Bromine Protected PSEPVE of Example 7, dimethoxyethane (20 mL), and lithium hydride (0.075 g, 9.5 mequiv.) The mixture is cooled to ca. −20°, then stirred while malononitrile is added as a solution in dimethoxyethane. After 18 hr, the mixture is filtered and evaporated. Following the method of Example 7, Zn powder is added to the reaction mixture to regenerate the olefinic bond.

Example 17

0.50 grams of the ionomer of Example 14 were mixed in powder form at 120° C. using a spatula with 0.5 grams of an ionomer comprising monomer units of VF2 and 9.5 mol-% of the lithium sulfonate form of PSEPVE prepared as described in copending application Ser. No. 98/23244 and 2.0 grams of a 1:1 by volume mixture of ethylene carbonate and gamma-butyrolactone, both reagents Selectipur grade from EM Industries). The mixture so formed was heated under nitrogen in a sealed glass vial to 100° C. for several hours until a homogenous, clear mixture resulted.

This mixture was then cooled to form a gel. About 0.5 g of the gel was removed from the glass vial and placed between two sheets of Kapton® polymide film (DuPont) and the combination placed between the platens of a Carver Hydraulic Unit Model #3912 preheated to 105° C., and was pressed at 1000 lbs ram force. The film that resulted was clear and uniform and 4.2–4.7 mils in thickness.

Once cooled to room temperature, a 1.0 cm by 1.5 cm membrane sample from this hot pressed film was cut using a knife and then tested using the four-point-probe test described above. Solvent uptake was nominally 200% based on the as-prepared composition of the film. Conductivity was $8.27 \times 10^{-4}$ S/cm.

An 18 mm diameter circular specimen was punched from the melt pressed film to serve as a battery separator membrane as hereinbelow described.

To form a cathode, the following materials were weighed and hand-mixed in a 50-ml glass jar inside a glove box under a dry nitrogen atmosphere:

0.625 grams (2.5 wt %) of Kynar Flex ® 2801 polyvinylidene fluoride, from Atochem.
1.75 grams (7.0 wt %) of the ionomer of Example 14
15.5 grams (62 wt %) of LiCoO$_2$, from EM Industries.
1.625 grams (6.5 wt %) of Super P carbon black from MMM Carbon.
5.5 grams (22 wt %) of a 1:1 by volume mixture of ethylene carbonate and gamma-butryolactone (GBL), both Selectipur Grade, EM Industries The mixture so formed was fed to the feed throat of a CSI-Max extruder, model CS-194. Extrusion conditions were as follows:

| Rotor temperature: | 110° C. |
| Header temperature: | 110° C. |
| Gap between rotor and header: | 0.13 cm |
| Rotor speed: | 192 rpm. |

The thus melt-compounded material was extruded through a circular die with a diameter of 0.32 cm, and was collected in a glass jar purged with dry nitrogen.

A 1.0 gram quantity of the extrudate was was melt-pressed between the platens of the Carver press at 110° C. and 20 klbs ram force inside a nitrogen-purged glove box, followed by cooling and release of pressure thereby forming a film of 5 mil thickness. A 12 mm diameter circular specimen was punched out of the film so formed.

The separator and cathode films prepared as hereinabove described were each exposed for 2 hours to an electrolyte solution composed of 1.0 M LiPF$_6$ in 1:1 EC/GBL by immersion in 2–4 ml of solution in a sealed glass vial for two hours.

The so-treated cathode and separator film were assembled into size 2325 coin cells with 3 layers of 4 mil thick lithium metal as the negative electrode. The coin cell was cycled at the C/5 rate for both charge and discharge at room temperature between the voltage limits of 4.2 V and 2.8 V. Capacity during the first charge for the LiCoO$_2$ cathode was 157.2 mAh/g, while capacity for the first discharge was 149.7 mAh/g, giving a reversibility of 95.2%. Capacity on the tenth discharge was 147.1 mAh/g and the coin cell achieved nearly 100 cycles to 80% of its initial capacity.

Example 18

The MicroFluidizer™ of Example 3 was charged with a solution of 5 g ammonium perfluoro octanoate in 75 ml demineralized water. The pump was started and the fluids allowed to recycle to mix the surfactant solution. PSEPVE (25 g) was added to the reservoir and the system allowed to recycle for 20 min to produce a well dispersed translucent blue PSEPVE emulsion. The outflow was then directed to a 200 ml volumetric flask. After the reservoir was pumped down, 100 ml demineralized water was added and pumped through the system to flush the remaining PSEPVE emulsion through and bring the level in the volumetric flask up to the mark. The final PSEPVE emulsion contained 0.25 g/ml PSEPVE and was translucent blue.

A 4-L horizontal stainless-steel stirred polymerization reactor was flushed with nitrogen and conditioned by charging with 2 liters demineralized water, 5 g ammonium persulfate, 5 g ammonium perfluorooctanoate, then agitating at 150 rpm while heating the vessel contents to 100° C./15 min. The vessel was cooled, the contents dumped to waste and the vessel rinsed 3 times with 2 liters demineralized water.

The reactor was charged with 1.75 liter demineralized water. 4 ml of the PSEPVE emulsion prepared above and 20 g of ammonium perfluorooctanoate were combined in an additional 100 ml of distilled water and added to the reactor. The reactor was sealed and three times pressured with nitrogen to 100 psig and vented. Three times the reactor was evacuated to −14 psig and flushed with vinylidene fluoride (VF2) to 0 psig. Agitation at 200 rpm was started and the reactor temperature was brought to 60° C. The reactor was pressurized with VF2 to 300 psig at which time 20 ml of 4.5% potassium persulfate solution was pumped in at 10 ml/min. The polymerization initiated in 0.03 hr. VF2 and the PSEPVE emulsion were fed as needed at a 99:1 mole ratio of VF2:PSEPVE to maintain 300 psig reactor pressure. The polymerization was continued for 3.2 hr, feeding a total of 251 g VF2/PSEPVE for an overall rate of 80 g/hr. The run was terminated to yield a milky-white latex containing 11.5% polymer solids. A total of 5 runs were made by repeating this process. The latex from these runs were combined and mixed by stirring to form a homogeneous blend.

The combined polymer latex was frozen in dry ice and defrosted. The agglomerated polymer was white and powdery. The polymer was washed vigorously 4 times in 5 gal of 50° C. tap water then washed a final time in 5 gal demineralized water (20° C.). The washed polymer was dried at 100° C. for 48 hr under nitrogen sparged partial vacuum to yield 1028 g of fine white polymer powder. $^{19}$F NMR analysis (DMF$_d$) was consistent with 0.9 mole % PSEPVE in the copolymer. DSC analysis indicated a glass transition temperature centered at Tg=−38° C. and a melting endotherm at Tm=162° C.

A 4-neck, 5 L flask maintained under dry, inert atmosphere was charged with 400 g of the 0.9 mol % VF$_2$/PSEPVE copolymer made above, 1.14g of lithium hydride, and 1600 ml of THF. The stirred mixture was cooled to ca. 5° C., and 100 ml of a THF solution containing 4.71 g of malononitrile was added dropwise over a ca. 20 min period. Temperature was maintained below 10° C. during addition. Mixture was allowed to warm to room temperature after addition was complete. After 20 hr, the mixture was cooled to 5°, treated with water (dropwise at first; then in portions so that total water added was 2500 mL during a 0.5 hr period).

The pH was adjusted to 7.1 by addition of dilute acetic acid. Another 750 mL water was added and the mixture was allowed to settle. Supernatant was removed using a siphon and product was washed with water. Product was filtered through a cloth filter membrane and washed with water to remove residual THF. The product was allowed to air-dry followed by drying under vacuum at 118° C. to provide 386.6 g of product.

$^{19}$F NMR (DMF-d7) showed: −76.5 to −80.0 (m, CF$_3$ and OCF$_2$, a=7.00), −91 to −95.0 (m, with major signals at −91.5,−94.7, (CH$_2$CF$_2$, a=203.21), −109 to −117 (m, with major signals at −113.5 and −115.9 (VF2 reversals), a=22.66), −122 to −127 (m, a=1.92), −144 (m, CF, a=1.17), consistent with 0.9 mol % comonomer content corresponding to the lithium methide derivative of PSEPVE.

A 1:1 (weight ratio) of ethylene carbonate/propylene carbonate (EC/PC) solution was prepared by dissolving 100 g of ethylene carbonate (EM Industries, Selectipur® grade) in 100 g of propylene carbonate (EM Industries, Selectipur® grade) at room temperature inside a nitrogen gas dry box.

The following was performed in a nitrogen gas dry box at <1 ppm moisture level. 0.5 g of the 0.9 mole % PSVF2-methide copolymer powder prepared above, and 0.5 g of the EC/PC solution were mixed inside a small vial. A portion of the mixture was then placed between two Kapton® polyimide sheets to be calendered into a film using a heated laminator. The laminator was located inside the dry box. It consisted of two heated steel rolls each of 102 mm diameter. At the front of the nip of the heated rolls was a preheat zone. The mixture was held in the preheat zone at 130° C. for about 2 minutes. The copolymer mixture was then passed through the heated rolls at 125° C. and at a speed of about 0.1 m/min. A force of about 1680 N was applied on the steel rolls. Two brass shims of 0.102 mm thick was placed, one on each side of the copolymer mixture, and fed simultaneously with the copolymer into the nip of the steel rolls to limit the minimum gap between the steel rolls. A stand-alone film of 0.083 mm thickness was formed.

A rectangular test section of this film was cut. The conductivity of this sample was determined using the 4-point-probe conductivity method of Doyle et al, WO98/20573. The conductivity of the sample was 0.067 mS/cm.

What is claimed is:

1. An ionic polymer (ionomer) comprising monomer units of vinylidene fluoride and further comprising 05–50 mol-% of trifluoroethylene monomer units having pendant groups comprising the radical represented by the formula $$—(OCF_2CFR)_aOCF_2(CFR')_bSO_2X\text{-}(M^+)(Y)(Z)_c \quad (I)$$

wherein

R and R' are independently selected from F, Cl or a perfluoroalkyl group having 1 to 10 carbon atoms optionally substituted by one or more ether oxygens;

a=0, 1 or 2;

b=0 to 6;

$M^+$ is $H^+$ or a univalent metal cation; X is C or N with the proviso that c=1 when X is C and c=0 when X is N;

when c=1, Y and Z are electron-withdrawing groups selected from the group consisting of CN, $SO_2R_f$, $SO_2R^3$, $P(O)(OR^3)_2$, $CO_2R^3$, $P(O)R^3_2$, $C(O)R_fC(O)R^3$, and wherein $R_f$ is a perfluoroalkyl group of 1–10 carbons optionally substituted with one or more ether oxygens;

$R^3$ is an alkyl group of 1–6 carbons optionally substituted with one or more ether oxygens, or an aryl group optionally further substituted;

Y and Z are the same or different;

or, when c=0, Y may be an electron-withdrawing group represented by the formula —$SO_2R_f'$ where $R_f'$ is the radical represented by the formula —$(R_f''SO_2N^-(M^+)SO_2)_mR_f'''$ where m=0 or 1, and $R_f''$. is —$C_nF_{2n}$— and $R_f'''$ is —$C_nF_{2n+1}$ where n=1–10, optionally substituted with one or more ether oxygens said ionomer being characterized by a melting point of greater than or equal to 150° C.

2. A process for making a methide ionomer the process comprising, combining in an inert organic liquid at a temperature in the range of 0–150° C. a copolymer comprising monomer units of vinylidene fluoride and 0.5–50 mol-% of monomer units represented by the formula:

$$CF_2=CF(OCF_2CFR)_aOCF_2(CFR')_bSO_2F \quad (III)$$

wherein R and R' are independently selected from F, Cl or a perfluoroalkyl group having 1 to 10 carbon atoms optionally substituted with one or more ether oxygens, a=0, 1 or 2, and b=0 to 6; with a carbanion derived from a methylene compound represented by the formula $CH_2YZ$ wherein Y and Z are electron-withdrawing groups selected from the group consisting of CN, $SO_2R_f$, $SO_2R^3$, $P(O)(OR^3)_2$, $CO_2R^3$, $P(O)R^3_2$, $C(O)R_fC(O)R^3$, and cycloalkenyl groups formed therewith, wherein $R_f$ is a perfluoroalkyl group of 1–10 carbons, optionally substituted with one or more ether oxygens, $R^3$ is an alkyl group of 1–6 carbons, optionally substituted with one or more ether oxygens or an aryl group optionally further substituted; and wherein Y and Z may be either the same or different to form a reaction mixture; reacting said reaction mixture until the desired degree of conversion has been achieved; and, removing the bulk of said organic liquid said ionomer being characterized by a melting point of greater than or equal to 150° C.

3. A process for forming an ionomer, the process comprising combining in an aqueous reaction medium vinylidene fluoride with an ionic monomer represented by the formula $$CF_2=CF—(OCF_2CFR)_aOCF_2(CFR')_bSO_2X^-(M^+)(Y)(Z)_c$$

wherein

R and R' are independently selected from F, Cl or a perfluoroalkyl group having 1 to 10 carbon atoms optionally substituted with one or more ether oxygens;

a=0, 1 or 2;

b=0 to 6;

$M^+$ is $H^+$ or a univalent metal cation;

X is C or N with the proviso that c=1 when X is C and c=0 when X is N;

when c=1, Y and Z are electron-withdrawing groups selected from the group consisting of CN, $SO_2R_f$, $SO_2R^3$, $P(O)(OR^3)_2$, $CO_2R^3$, $P(O)R^3_2$, $C(O)R_fC(O)R^3$, and cycloalkenyl groups formed therewith wherein $R_f$ is a perfluoroalkyl group of 1–10 carbons optionally substituted with one or more ether oxygens;

$R^3$ is methyl or ethyl;

Y and Z are the same or different;

or, when c=0, Y may be an electron-withdrawing group represented by the formula —$SO_2R_f'$ where $R_f'$ is the radical represented by the formula —$(R_f''SO_2N^-(M^+)SO_2)_mR_f'''$ where m=0 or 1, and $R_f''$ is —$C_nF_{2n}$- and $R_f'''$ is $C_nF_{2n+1}$ where n=1–10, optionally substituted by one or more ether oxygens, to form a reaction mixture;

introducing a free radical initiator;

reacting said reaction mixture to form an ionomer having a melting point of 150° C. or greater.

4. The ionomer of claim 1 wherein $M^+$ is an alkali metal cation.

5. The process of claims 2 or 3 wherein $M^+$ is an alkali metal cation.

6. The ionomer of claim 1 wherein $M^+$ is a lithium cation.

7. The process of claim 5 wherein $M^+$ is a lithium cation.

8. The ionomer of claim 1 wherein Y and Z are —CN or —$CO_2C_2H_5$ when c=1, and Y is —$SO_2CF_3$ or Y is —$SO_2C_2F_5$ when c=0.

9. The Process of claim 3 wherein Y and Z are —CN or —$CO_2C_2H_5$.

10. The process of claim 3 wherein Y and Z are —CN or —CO$_2$CH$_3$ when c=1, and Y is —SO$_2$CF$_3$ or Y is —SO$_2$C$_2$F$_5$ when c=0.

11. The ionomer of claim 4 or claim 8 wherein R is trifluoromethyl, R' is F, a=1, and b=1.

12. The process of claim 5 wherein R is trifluoromethyl, R' is F, a=1, and b=1.

13. A conductive composition comprising the ionomer of claim 1 or claim 11 and a liquid imibibed therewithin.

14. The ionomer of claim 1 or claim 11 wherein the concentration of ionic monomer units is 3 to 12 mol %.

15. The ionomer of claim 1 in the form of a film or sheet.

16. The ionomer of claim 1 further comprising up to 30 mol % of one or more additional monomer units selected from the group consisting of tetrafluoroethylene, chlorotrifluoroethylene, ethylene, hexafluoropropylene, trifluoroethylene, vinyl fluoride, vinyl chloride, vinylidene chloride, and perfluoroalkylvinyl ethers of the formula CF$_2$=CFOR$_f$ where R$_f$=CF$_3$, C$_2$F$_5$ or C$_3$F$_6$.

17. The ionomer of claim 16 wherein the additional monomer units are selected from the group consisting of tetrafluoroethylene, hexafluoropropylene, ethylene, and perfluoroalkylvinyl ethers.

18. The ionomer of claim 1 further comprising inorganic particles admixed therewith.

19. The ionomer of claim 18 wherein the inorganic particles are silica particles of less than 1.0 micrometer in diameter, the silica being present in the admixture at up to 50% by weight of the total.

20. The conductive composition of claim 13 wherein the liquid is a protic liquid.

21. The conductive composition of claim 20 wherein the liquid is selected from the group consisting of water or methanol.

22. The conductive composition of claim 13 wherein the liquid is an aprotic liquid.

23. The conductive composition of claim 13 wherein the liquid is selected from the group consisting of organic carbonates and mixtures thereof.

24. The conductive composition of claim 23 wherein the liquid is a mixture of ethylene carbonate and at least one liquid selected from the group consisting of propylene carbonate, gamma butyrolactone, dimethyl carbonate, methyl ethyl carbonate and diethyl carbonate.

25. The conductive composition of claim 13 in a form selected from the group consisting of a film, sheet and gel.

26. An electrode comprising at least one electrode active material and the conductive composition of claim 15.

27. The electrode of claim 26 wherein R is trifluoromethyl, a=1, M$^+$ is a lithium cation, the molar concentration of the ionic pendant group in the ionomer is in the range of 3–12 mol-%, and the liquid is selected form the group of organic carbonates and mixtures thereof.

28. The electrode of claim 26, further comprising carbon black, wherein the weight ratio of ionomer to electrode active material is between 0.05 and 0.8 and the weight ratio of carbon black to electrode active material is between 0.01 and 0.2.

29. An electrochemical cell comprising a positive electrode, a negative electrode, a separator disposed between the positive and negative electrodes, and a means for connecting the cell to an outside load or source wherein at least one of the group consisting of the separator, the cathode, and the anode, comprises the ionic polymer of claim 1.

30. An electrochemical cell of claim 29 further comprising a liquid selected from the group consisting of organic carbonates and mixtures thereof, the liquid being imbibed in the ionomer.

* * * * *